(12) United States Patent
Park et al.

(10) Patent No.: US 11,241,459 B2
(45) Date of Patent: Feb. 8, 2022

(54) TREATING LIVER FIBROSIS USING ADIPOSE STEM CELL-DERIVED EXOSOMES AS ACTIVE INGREDIENT

(71) Applicant: ExoStemTech Co., Ltd., Ansan (KR)

(72) Inventors: Jae Hyung Park, Suwon (KR); Hansang Lee, Yongin (KR); Roun Heo, Suwon (KR); Hwa Seung Han, Suwon (KR)

(73) Assignee: ExoStemTech Co., Ltd., Ansan (KR)

( * ) Notice: Subject to any disclaimer, the term of this patent is extended or adjusted under 35 U.S.C. 154(b) by 241 days.

(21) Appl. No.: 16/462,501

(22) PCT Filed: Nov. 21, 2017

(86) PCT No.: PCT/KR2017/013255
§ 371 (c)(1),
(2) Date: May 20, 2019

(87) PCT Pub. No.: WO2018/093233
PCT Pub. Date: May 24, 2018

(65) Prior Publication Data
US 2019/0314419 A1 Oct. 17, 2019

(30) Foreign Application Priority Data

Nov. 21, 2016 (KR) .......................... 10-2016-0155121
Nov. 20, 2017 (KR) .......................... 10-2017-0154641

(51) Int. Cl.
*A61K 35/28* (2015.01)
*A23L 33/10* (2016.01)
*A61P 1/16* (2006.01)

(52) U.S. Cl.
CPC .............. *A61K 35/28* (2013.01); *A23L 33/10* (2016.08); *A61P 1/16* (2018.01); *A23V 2002/00* (2013.01); *A23V 2200/32* (2013.01)

(58) Field of Classification Search
None
See application file for complete search history.

(56) References Cited

U.S. PATENT DOCUMENTS

| | | | |
|---|---|---|---|
| 2014/0234276 A1 | 8/2014 | Germann et al. | |
| 2016/0206661 A1 | 7/2016 | Fraser et al. | |
| 2016/0272936 A1 | 9/2016 | Lee et al. | |
| 2018/0273906 A1* | 9/2018 | Ashraf | A61K 31/27 |

FOREIGN PATENT DOCUMENTS

| | | |
|---|---|---|
| EP | 3494977 A1 | 6/2019 |
| KR | 20080101140 | 11/2008 |
| KR | 101542849 | 8/2015 |
| KR | 20160055827 | 5/2016 |
| WO | WO2013017699 A1 | 2/2013 |

OTHER PUBLICATIONS

Duong, et al., "The Use of Nanoparticles to Deliver Nitric Oxide to Hepatic Stellate Cells for Treating Liver Fibrosis and Portal Hypertension," Small, 2015, vol. 11 (19), pp. 2291-2304.
Harn, et al., "Adipose-Derived Stem Cells Can Abrogate Chemical-Induced Liver Fibrosis and Facilitate Recovery of Liver Function," Cell Transplant., 2012, vol. 21 (12), pp. 2753-2764.
Hu, et al., "Exosomes Derived from Human Adipose Mensenchymal Stem Cells Accelerates Cutaneous Wound Healing via Optimizing the Characteristics of Fibroblasts," Scientific Reports, 2016, vol. 6, pp. 11, https://www.nature.com/articles/srep32993.
Jang, et al., "Effect of Bone Marrow-Derived Mesenchymal Stem Cells on Hepatic Fibrosis in a Thioacetamide-Induced Cirrhotic Rat Model," BMC Gastroenterol., 2014, vol. 14 (198), pp. 12.
Li, et al., "Exosomes Derived from Human Umbilical Cord Mesenchymal Stem Cells Alleviate Liver Fibrosis," Stem Cells Dev., 2013, vol. 22 (6), pp. 845-854.
Marote, et al., "MSCs-Derived Exosomes: Cell-Secreted Nanovesicles with Regenerative Potential," Front Pharmacol., 2016, vol. 7, pp. 8.
Search Report dated Feb. 28, 2018 for PCT Application No. PCT/KR2017/013255.
Qu et al., "Exosomes derived from miR-181-5p-modified adipose-derived mesenchymal stem cells prevent liver fibrosis via autophagy activation," J. Cell. Mol. Med., 2017, vol. 21, No. 10, pp. 2491-2502.

* cited by examiner

*Primary Examiner* — Ralph J Gitomer

(57) ABSTRACT

The present embodiment relates to a composition containing human adipose stem cell-derived exosomes as an active ingredient for preventing, alleviating or treating liver fibrosis. The adipose stem cell-derived exosomes according to the present embodiment carry genetic information, protein, growth factor and the like for treating liver fibrosis, and have shown excellent results in treating liver fibrosis in animal models therefor, and, being a cell-derived substance, exosomes have the advantages of being highly biocompatible and having a superb absorption rate.

4 Claims, 9 Drawing Sheets

(8 of 9 Drawing Sheet(s) Filed in Color)

[FIG. 1]
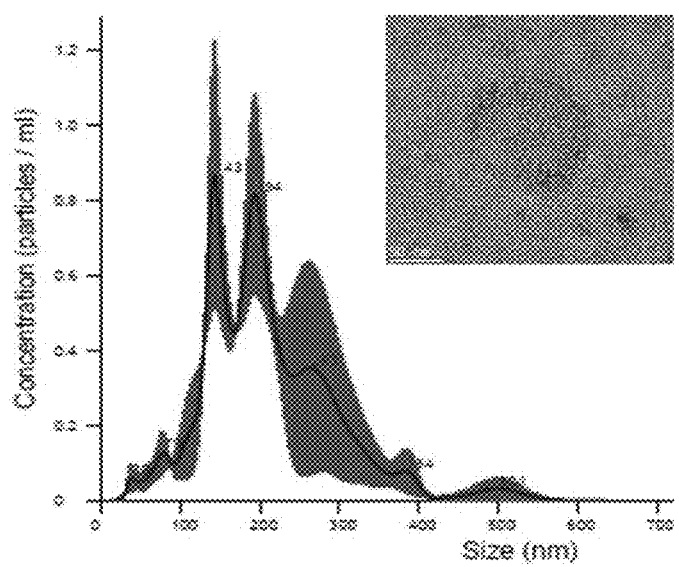
[FIG. 2]
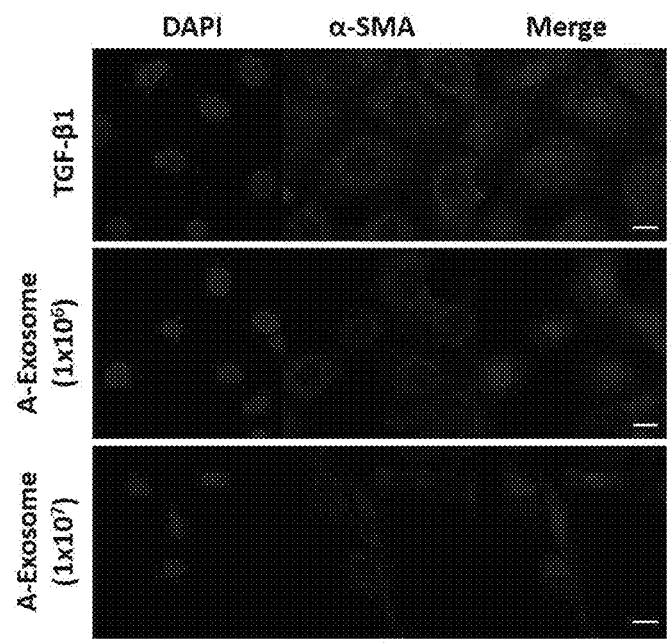

[FIG. 3]
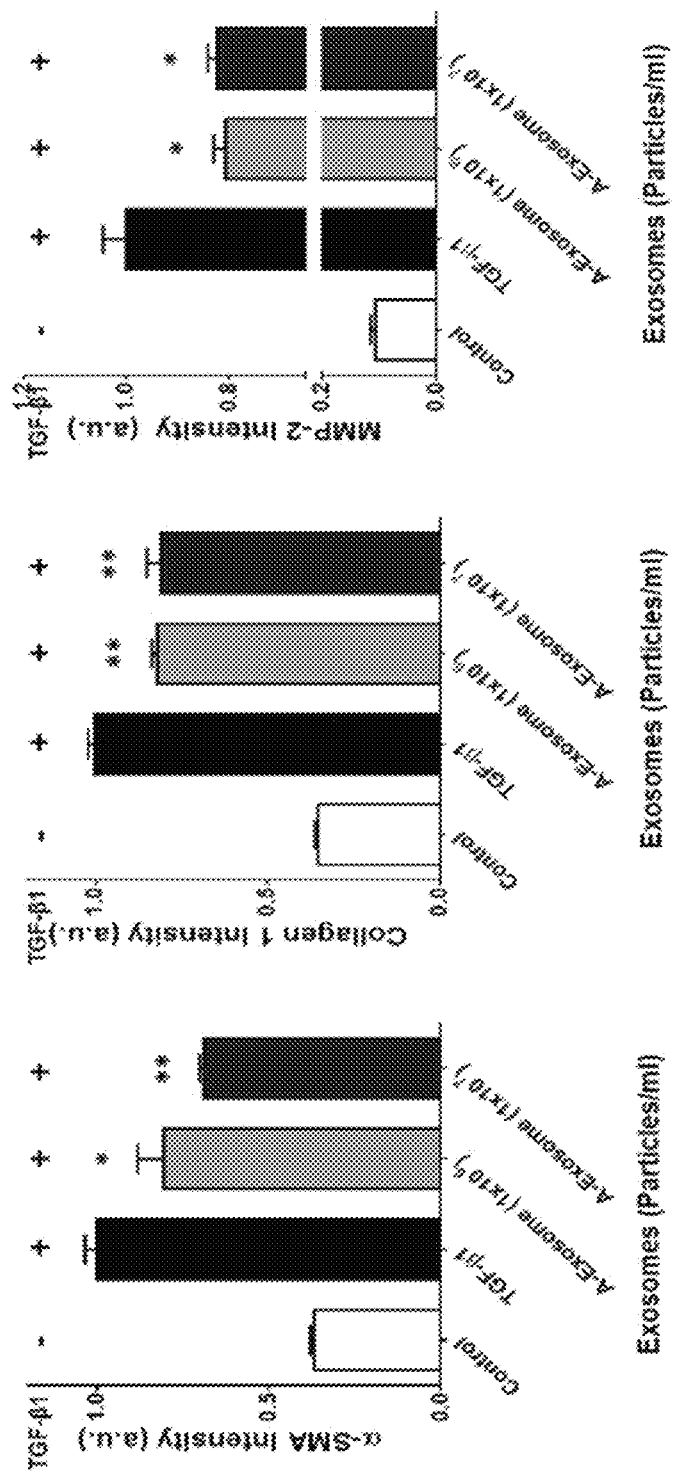

[FIG. 4]
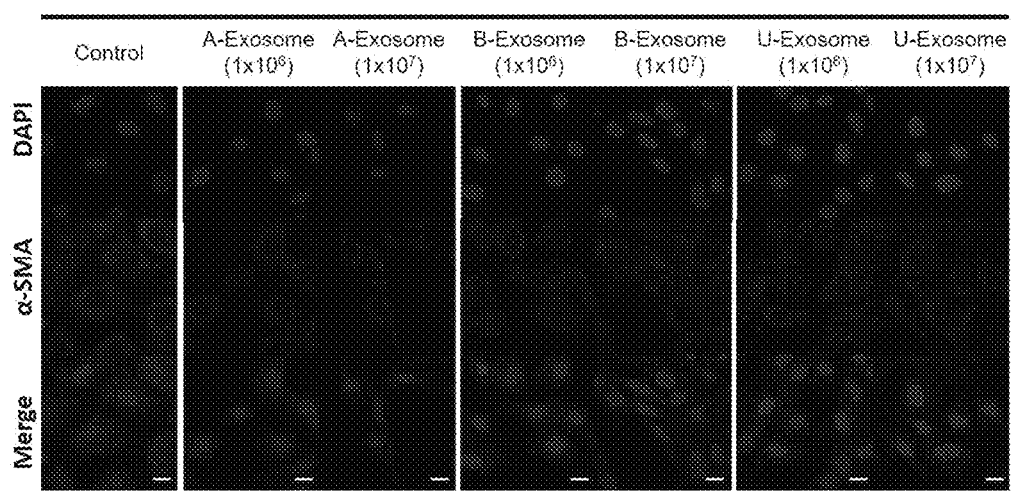

[FIG. 5]
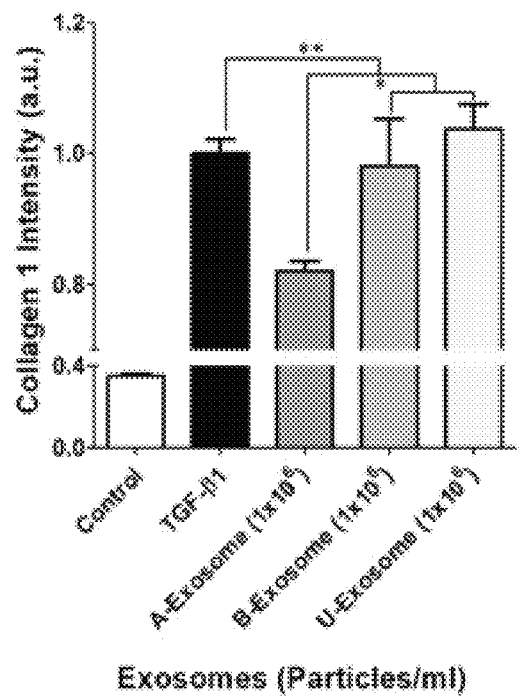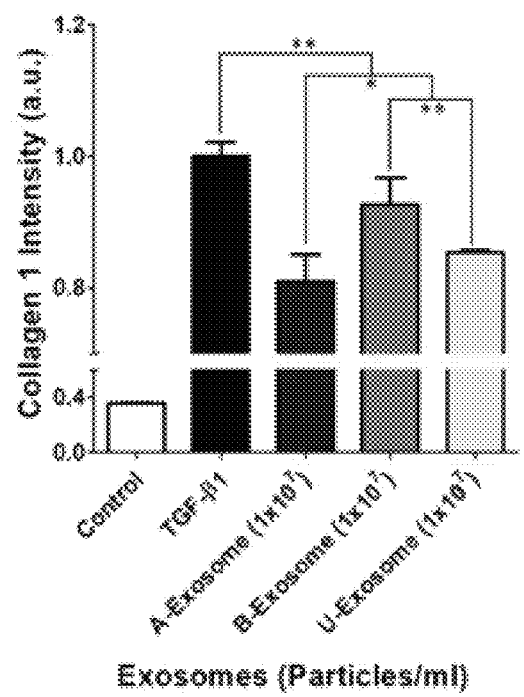

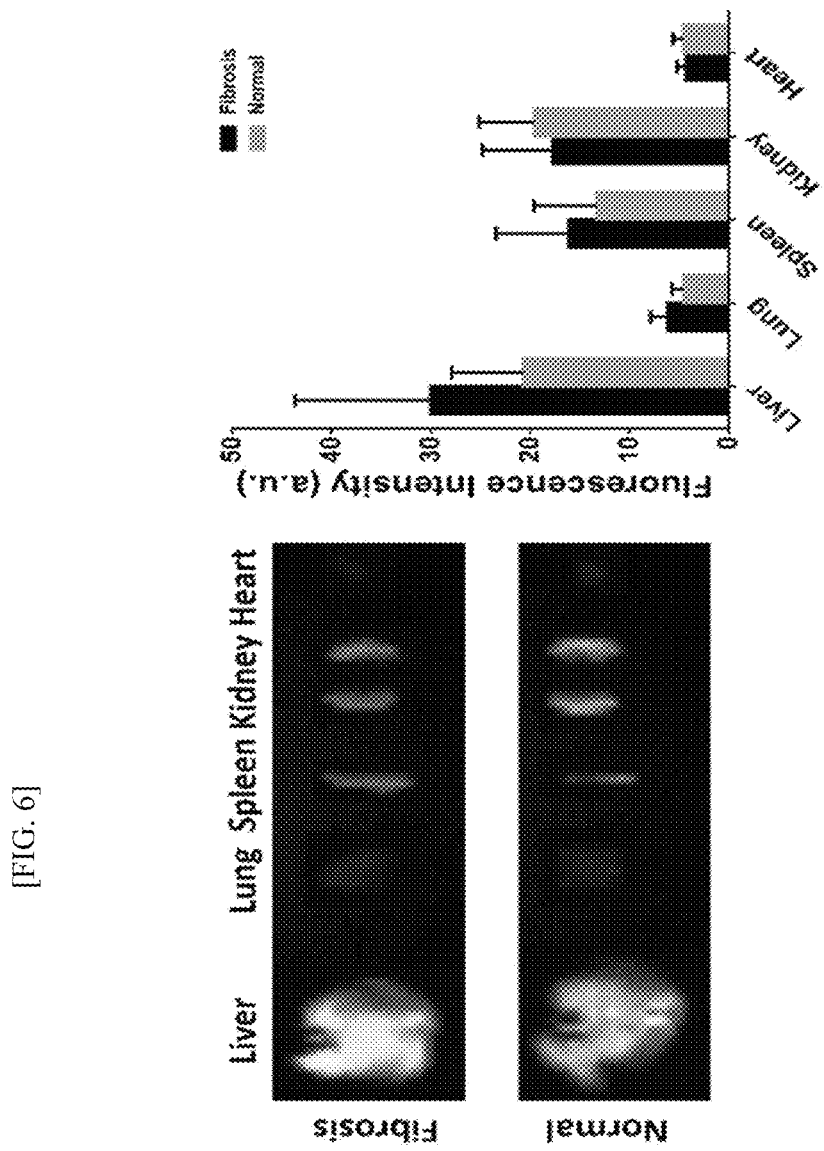
[FIG. 6]

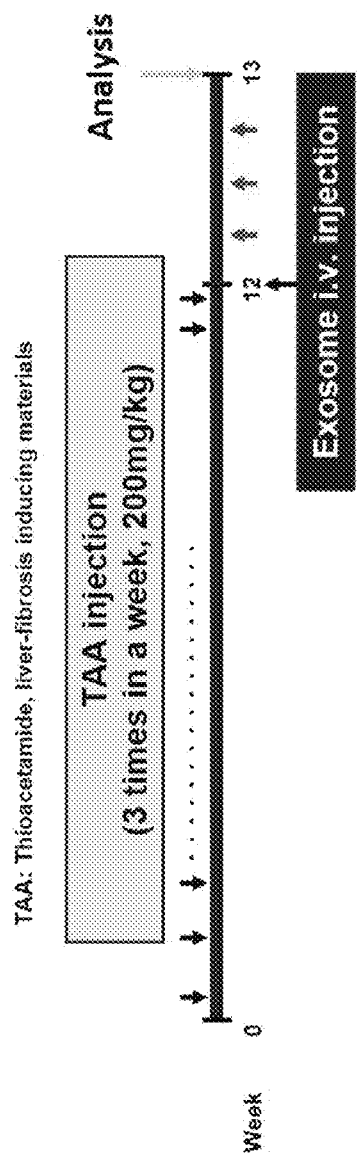
[FIG. 7]

[FIG. 8]
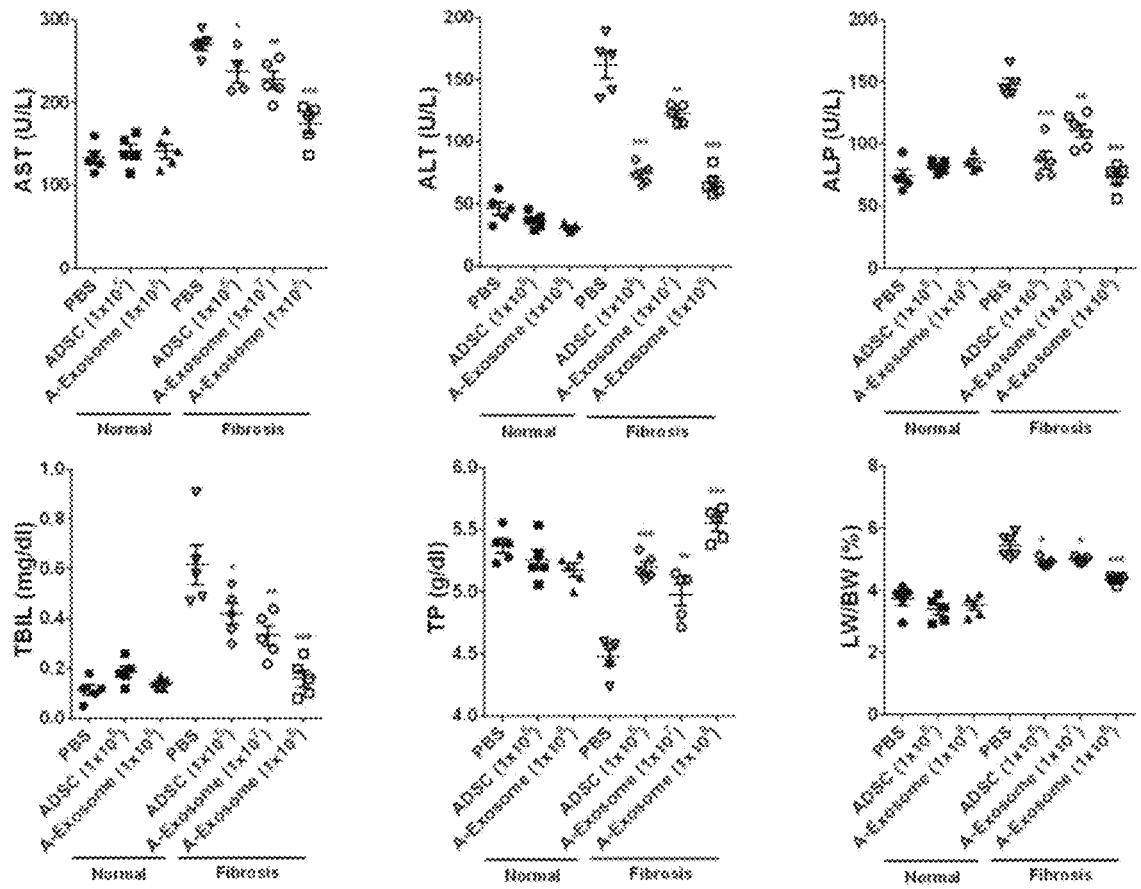
[FIG. 9a]
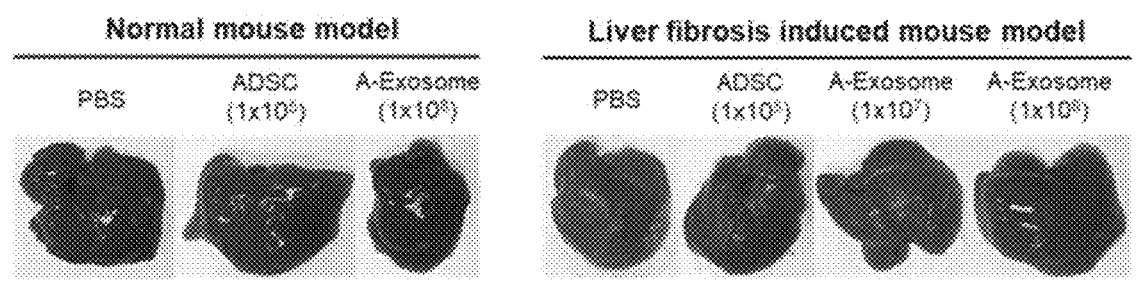

[FIG. 9b]
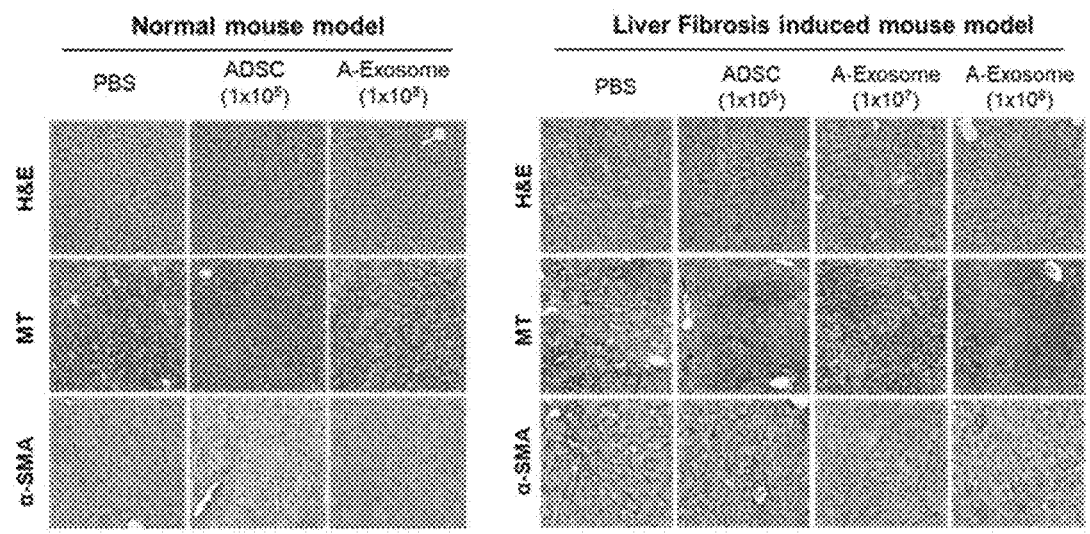

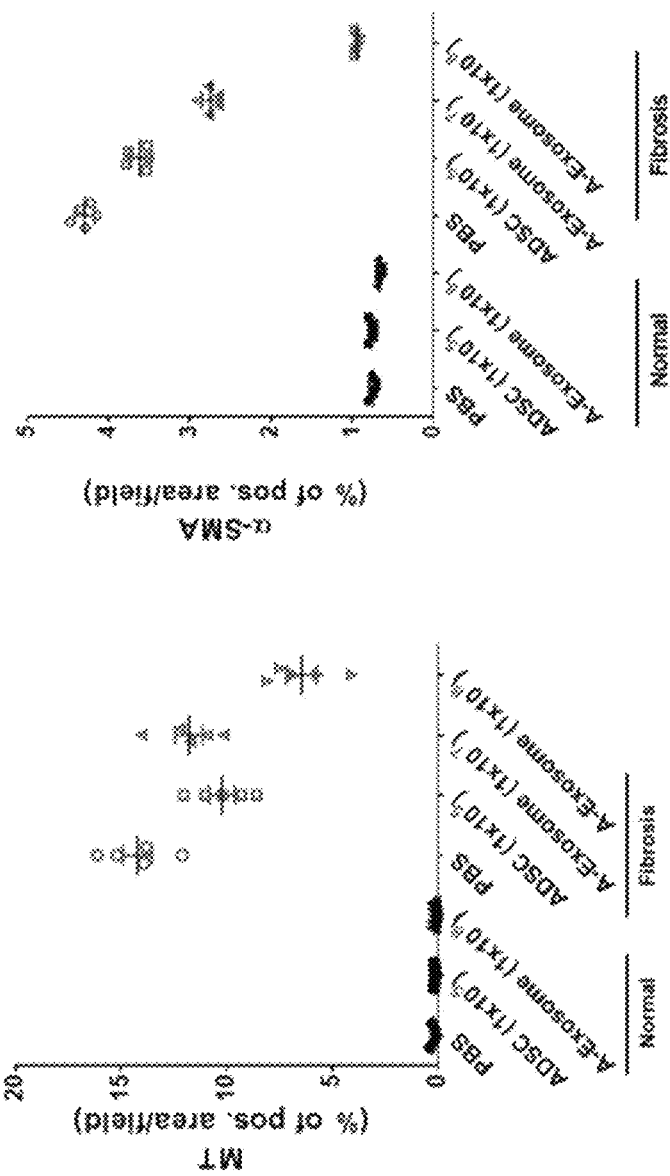
[FIG. 9c]

TREATING LIVER FIBROSIS USING ADIPOSE STEM CELL-DERIVED EXOSOMES AS ACTIVE INGREDIENT

CROSS-REFERENCE TO RELATED APPLICATIONS

This application is a U.S. National Phase of International Application No. PCT/KR2017/013255, filed Nov. 21, 2017 which claims priority to Korean Application No. 10-2016-0155121, filed Nov. 21, 2016 and 10-2017-0154641, filed Nov. 20, 2017.

TECHNICAL FIELD

The present embodiment relates to a composition for preventing, alleviating or treating liver fibrosis.

BACKGROUND ART

Liver fibrosis is caused by excessive deposition of extracellular matrix due to chronic inflammation, and if such a chronic liver disease persists, it may be progressed to liver cirrhosis due to structural transformation in liver and decrease of the number of hepatic cells. This chronic liver disease can be considered as a continuous disease progressing from chronic B type or C type hepatitis, chronic hepatitis due to continuous excessive drinking and use of liver toxic materials, etc., through fibrosis, to liver cirrhosis, rather than as an independent disease.

Currently, treatment for hepatitis and liver cirrhosis is for slowing the progress of symptoms and deterioration of liver function caused thereby, and there is a method of using drugs such as peginterferon or antiviral agents depending on causes in case of liver cirrhosis and reaching a complete recovery through liver transplantation in severe cases. However, in the case of drug treatment, treatment resistance may occur and liver transplantation has a limitation in that it should endure donor insufficiency and risk and cost of surgery, and thus the need for a new therapeutic method has emerged.

The liver regeneration therapeutic method using stem cells is a therapeutic method which has received much attention in recent years, and it is known that injected stem cells show a therapeutic effect by differentiating into functional hepatic cells in damaged liver and reconstituting. Up to now, the results of differentiation of stem cells into functional hepatic cells with high efficiency in vitro (Korean Patent No. 10-1542849) have been reported, but there is a problem in that the efficiency of hepatic cell differentiation is actually low, when stem cells are transplanted into animal models or humans. Furthermore, there is a disadvantage that stem cells which proliferate and differentiate into hepatic cells are not known accurately, since the accurate marker of liver stem cells is not defined.

In addition, generally, the biggest problem of the conventional treatment using stem cells is that the accurate efficacy cannot be demonstrated, as the engraftment rate and survival rate of cells in the body are not consistent depending on patients, and also, the possibility of cancerization of stem cells cannot be excluded, and as the culture solution containing various growth factors secreted from stem cells comprises various cell wastes as well as growth factors, it may cause potential problems.

Therefore, a new therapeutic approach is needed to solve the limitations of treatment of liver diseases using stem cells.

DISCLOSURE

Technical Problem

In order to solve the above conventional problems, the present inventors evaluated the therapeutic effect on liver fibrosis using exosomes isolated from human adipose stem cells, and confirmed the excellent therapeutic effect by administration of the exosomes in human hepatic stellate cells and liver fibrosis animal models, and on this basis, the present embodiment has been completed.

Accordingly, an object of the present embodiment is to provide a composition for preventing, alleviating or treating liver fibrosis, containing adipose stem cell-derived exosomes as an active ingredient.

However, the technical problem to be solved by the present embodiment is not limited to the above-mentioned problems and other matters not mentioned can be clearly understood by those skilled in the art from the following description.

Technical Solution

In order to achieve the object of the present embodiment, the present embodiment provides a pharmaceutical composition for preventing or treating, containing adipose stem cell-derived exosomes as an active ingredient.

In addition, the present embodiment provides a health functional food composition for alleviating liver fibrosis, containing adipose stem cell-derived exosomes as an active ingredient.

As one example of the present embodiment, the adipose stem cell may be a human adipose stem cell.

As another example of the present embodiment, the composition may reduce a level of aspartate aminotransferase (AST), alanine aminotransferase (ALT), alkaline phosphatase (ALP), total bilirubin (TP), or LW/BW (Ratio of liver weight to body weight) in blood.

In addition, the present embodiment provides a method for preventing or treating liver fibrosis, comprising a step of administering a pharmaceutical composition containing adipose stem cell-derived exosomes as an active ingredient to a subject.

Moreover, the present embodiment provides a use of preventing or treating liver fibrosis, of adipose stem cell-derived exosomes.

Advantageous Effects

The adipose stem cell-derived exosomes according to the present embodiment carry genetic information, protein, growth factor and the like for treating liver fibrosis, and have shown excellent results in treating liver fibrosis in animal models therefor, and, being a cell-derived substance, exosomes have the advantages of being highly biocompatible and having a superb absorption rate.

Accordingly, the limits of medicine in current use can be overcome, and side effects that can arise due to cancerization of stem cells or cell waste products in treatments using stem cells themselves can be minimized. In addition, the delivery to the liver can be natural via intravenous injection, local injection and the like which can be applied simply without surgery, thus economic cost can be reduced.

In conclusion, the adipose stem cell-derived exosomes according to the present embodiment are expected to be effectively used for preventing, alleviating and treating liver fibrosis.

BRIEF DESCRIPTION OF DRAWINGS

The patent or application file contains at least one drawing executed in color. Copies of this patent or patent application publication with color drawing(s) will be provided by the Office upon request and payment of the necessary fee.

FIG. 1 is the result of confirming physical and biochemical properties of exosomes isolated from human adipose stem cells using an electron microscope and a nanoparticle tracking analyzer.

FIG. 2 shows the result of confirming reduction of α-SMA expression level by treating human adipose stem cell-derived exosomes (A-Exosome), in order to confirm α-smooth smooth muscle actin (α-SMA) expressed in LX-2 that is an activated hepatic stellate cell induced by TGF-β1.

FIG. 3 is the result of progressing the real-time polymerase chain reaction evaluation, in order to confirm quantitative mRNA changes of LX-2 that is a hepatic stellate cell line related to liver fibrosis.

FIG. 4 is the result of confirming the expression level of α-SMA by progressing the immunofluorescence evaluation, in order to comparatively evaluate efficacies of human adipose stem cell-derived exosomes and other tissue stem cell-derived exosomes.

FIG. 5 is the result of confirming the expression level of Collagen 1 by progressing the real-time polymerase chain reaction evaluation, in order to comparatively evaluate efficacies of human adipose stem cell-derived exosomes and other tissue stem cell-derived exosomes.

FIG. 6 is the result of confirming the fluorescence by securing major organs at 24 hours after intravenously administering fluorescence-labeled human adipose stem cell-derived exosomes into each model, in order to confirm in vivo movements of human adipose stem cell-derived exosomes in the normal model and liver fibrosis-induced model.

FIG. 7 shows a mimetic diagram of the animal experiment established to confirm the anti-fibrosis effect of human adipose stem cell-derived exosomes in the liver fibrosis mouse model.

FIG. 8 is the result of measuring the levels of blood AST (Aspartate aminotransferase), ALT (Alanine aminotransferase), ALP (Alkaline phosphatase), TBIL (Total bilirubin), TP (Total protein) and LW/BW (Ratio of liver weight to body weight), by administering exosomes into the normal model and liver fibrosis mouse model three times and collecting blood 5 days after the first administration.

FIG. 9a is an image obtained by administering exosomes into the normal model and liver fibrosis mouse model certain times and extracting liver 5 days after the first administration and observing it with naked eyes.

FIG. 9b is the result of conducting H&E staining, Masson' trichrome (MT) staining and α-SMA staining for secured liver tissue and then observing it with an optical microscope.

FIG. 9c is a quantitative graph showing the amount of collagen and the amount of α-SMA by MT compared to the total area.

BEST MODE

The present embodiment is capable of applying various modifications and having various examples, and therefore specific examples are illustrated in the drawings and described in the detailed description in detail. However, it should be understood that this is not to limit the present invention to specific embodiments, but includes all modifications and equivalents to alternatives falling within the spirit and technical scope of the present invention. In describing the present invention, when it is judged that a detailed description of related prior art may obscure the gist of the present invention, the detailed description will be omitted.

The present inventors have intensively studied a way of overcoming problems of cell therapy using therapeutic drugs or stem cells themselves used currently in the treatment of liver fibrosis, and as a result, have confirmed the therapeutic effect of liver fibrosis of human adipose stem cell-derived exosomes, thereby completing the present embodiment.

Hereinafter, a pharmaceutical composition for preventing or treating liver fibrosis according to a specific embodiment of the invention will be described in more detail.

Specifically, in one embodiment of the present invention, human adipose stem cells were cultured and the cell culture supernatant was collected, and the exosomes secreted from the cells were separated and purified (See Example 1), and thereby the anti-fibrosis effect of the exosomes was confirmed through an in vitro cell experiment and an in vivo mouse model.

In addition, the expression level of α-SMA was confirmed by immunofluorescence evaluation using an optical microscope, and by quantitatively demonstrating the amount of fibrosis-related mRNA through real-time polymerase chain reaction, it was confirmed that the expression level of α-SMA was largely increased in a hepatic stellate cell activated by treating TGF-β1, and it was demonstrated that the expression level of α-SMA was significantly decreased as the treatment concentration of human adipose stem cell-derived exosomes was increased (See Example 2).

In addition, it was confirmed that the RNA amount of α-SMA, Collagen 1 and MMP-2 that were fibrosis-related factors was largely increased when the hepatic stellate cell was activated by treating TGF-β1, but when adipose stem cell-derived exosomes were treated by concentration under the same condition, it was significantly decreased, and it was confirmed that this tendency was more effective as the concentration of exosomes was increased (See Example 2).

On the other hand, as one embodiment of the present invention, the adipose stem cell may be a human adipose stem cell. The human adipose stem cell-derived exosomes can effectively alleviate liver fibrosis by reducing numerical values of fibrosis-related factors of hepatic stellate cells activated by fibrosis, compared to other tissue stem cell-derived exosomes.

In addition, to comparatively evaluate anti-fibrosis of human adipose stem cell-derived exosomes and other tissue stem cell-derived exosomes used in the present embodiment, it was observed that the human adipose stem cell-derived exosomes significantly reduced the fluorescence of α-SMA than umbilical-cord stem cell-derived exosomes or bone-marrow stem cell-derived exosomes which were other tissue stem cell-derived exosomes, and it was confirmed that the human adipose stem cell-derived exosomes can effectively alleviate liver fibrosis by reducing numerical values of fibrosis-related factors of hepatic stellate cells activated by fibrosis, compared to other tissue stem cell-derived exosomes (See Example 3).

On the other hand, the present embodiment provides a method for preventing or treating liver fibrosis, comprising a step of administering a pharmaceutical composition containing adipose stem cell-derived exosomes as an active ingredient to a subject.

The administration of human adipose stem cell-derived exosomes can not only effectively inhibit the formation of fibrous septa but also maintain the structural shape of hepatic cells well, and effectively inhibit fibrosis of liver tissue, thereby maintaining in a form of normal tissue well.

Meanwhile, human adipose stem cells and human adipose stem cell-derived exosomes have an effect of alleviating liver function, but when comparing both, the liver function can be more effectively alleviated in case of administering human adipose stem cell-derived exosomes than human adipose stem cell (See Example 5).

Furthermore, the pharmaceutical composition for preventing or treating liver fibrosis according to the present embodiment may reduce a level of blood aspartate aminotransferase (AST), blood alanine aminotransferase (ALT), alkaline phosphatase (ALP), total bilirubin (TP) or LW/BW (Ratio of liver weight to body weight).

Accordingly, the present embodiment provides a pharmaceutical composition for preventing or treating liver fibrosis containing adipose stem cell-derived exosomes as an active ingredient.

The term used herein, "prevent" means all actions of inhibiting liver fibrosis or delaying occurrence by administration of the pharmaceutical composition according to the present embodiment.

The term used herein, "treat" means all actions of improving or beneficially changing symptoms by liver fibrosis by administration of the pharmaceutical composition according to the present embodiment.

The term used herein, "stem cell" is a cell constituting a subject or a cell being a basis of tissue, and its characteristics mean a cell which is capable of self-renewal by repeated division and has multipotency that can differentiate into cells having a specific function according to the circumstance. It occurs in all tissues during the fetal development process, and it is also found in some tissues in which cells are actively replaced such as bone-marrow and epithelial tissue, etc. even in adult. Stem cells are classified into totipotent stem cells which are formed when the first division starts, pluripotent stem cells which are made by continuous division of the cells and are in the blastula endothelium, and multipotent stem cells which are present in mature tissues and organs. Then, the multipotent stem cells are cells which can differentiate only into cells specific to tissues and organs in which these cells are comprised, and are involved in the growth and development of each tissue and organ of fetal, neonatal and adult stages, as well as the function of maintaining homeostasis of adult tissues and inducing regeneration when tissues are damaged. These tissue-specific multipotent cells are collectively referred to as adult stem cells.

Mesenchymal stem cells classified into adult stem cells are cells spotlighted as materials of regenerative medicine, and they can be collected from tissues such as bone-marrow, cord blood, adipose tissue, umbilical-cord, etc., and they have differentiation potency into cells constituting various human body tissues such as adipose cells, osteocytes, cartilage cells, nerve cells, cardiac muscle cells, etc. different from blood stem cells. Stem cells separated from human adipose tissues were used in the present embodiment, but not limited thereto.

The term used herein, "exosome" is cell-derived vesicles present in almost all eukaryotic cytosol including blood, urine and culture solution of cells, and is known to have a diameter of 30 to 100 nm as average. The exosome has received attention as uses for biomarkers, diagnosis and treatment of specific diseases clinically, since it has been reported that it is secreted as fused to the plasma membrane or is directly secreted from the plasma membrane, and it performs an important specific function during processes such as aggregation, intracellular signaling, cell waste management, and the like. In the present embodiment, the exosome may be naturally secreted from human adipose stem cells by culturing the cells.

The pharmaceutical composition according to the present embodiment comprises adipose stem cell-derived exosomes as an active ingredient, and may comprise a pharmaceutically acceptable carrier. The pharmaceutically acceptable carrier is commonly used for formulation, and includes saline solution, sterilized water, Ringer's solution, buffer saline solution, cyclodextrin, dextrose solution, maltodextrin solution, glycerol, ethanol, liposome and the like, but not limited thereto, and may further comprise other common additives such as antioxidants, buffer solution, etc. if necessary. In addition, it may be formulated as formulations for injection such as aqueous solution, suspension, emulsion, etc., pills, capsules, granules or tablets, by additionally adding a diluent, a dispersant, a surfactant, a bonding agent, a lubricant, and the like. For suitable pharmaceutically acceptable carriers and formulation, it can be preferably formulated according to each component using the method disclosed in Remington's literature. The pharmaceutical composition of the present embodiment may be formulated as injections, inhalants, skin external preparations, or oral preparations, etc. without specific limitations.

The pharmaceutical composition of the present embodiment may be orally administered or parenterally administered (for example, intravenous, subcutaneous, dermal, nasal and airway application) according to the desired method, and the dose differs depending on conditions and body weight of patients, degree of disease, drug form, administration route and time, but may be properly selected by those skilled in the art.

The pharmaceutical composition according to the present embodiment is administered in a pharmaceutically effective amount. In the present embodiment, "pharmaceutically effective amount" means an amount enough to treat a disease at a reasonable benefit/risk ratio applicable for medical treatment, and the effective dose level may be determined according to factors including kinds of diseases of patients, severity, activity of drugs, sensitivity to drugs, administration time, administration route and emission ratio, treatment time, and simultaneously used drugs, and other factors well known in the medical field. The composition according to the present embodiment may be administered as an individual therapeutic agent, or be administered together with other therapeutic agents, and it may be administered sequentially or simultaneously with the conventional therapeutic agents, and it may be singly or multiply administered.

It is important to administer the amount in which the maximum effect can be obtained in a minimal amount without side effects, considering all the above factors, and it may be easily determined by those skilled in the art.

Specifically, the effective amount of the composition according to the present embodiment may differ according to the age, gender and body weight of patients, and in general, 0.001 to 150 mg, preferably 0.01 to 100 mg per body weight 1 kg may be administered daily or every other day, or may be administered 1 to 3 times a day. However, since it may be increased or decreased according to administration route, severity of obesity, gender, body weight, age, and the like, the dose does not limit the scope of the present embodiment by any method.

As other aspect of the present embodiment, the present embodiment provides a health functional food composition for alleviating liver fibrosis, containing adipose stem cell-derived exosomes as an active ingredient.

The term used herein, "alleviate" means all actions of at least reducing parameters related to conditions to be treated, for example, the degree of symptoms.

In the health functional food composition of the present embodiment, the active ingredient may be added to food as it is or may be used with other food or food components, and may be properly used according to the common methods. The amount of mixing of the active ingredient may be suitably determined according to its purpose of use. In general, in case of preparation of food or beverages, the composition of the present embodiment is added in an amount of 15% by weight or less, preferably 10% by weight or less, on the basis of raw materials. However, in the case of long-term consumption intended for health and hygiene purposes or for health control purposes, the amount may be less than or equal to the above range.

The health functional food composition of the present embodiment has no particular limitation on other components other than containing the active ingredient as an essential ingredient at the indicated ratio, and may contain various flavoring agents or natural carbohydrates, etc. as an additional ingredient, as same as common beverage. The examples of the afore-mentioned natural carbohydrates are common saccharides such as monosaccharides, for example, glucose, fructose, etc.; disaccharides, for example, maltose, sucrose, etc.; and polysaccharides, for example, dextrin, cyclodextrin, and sugar alcohols such as xylitol, sorbitol, erythritol, and the like. As flavoring agents other than those aforementioned, natural flavoring agents (thaumatin, stevia extract, for example, rebaudioside A, glycyrrhizin, etc.) and synthetic flavoring agents (saccharin, aspartame, etc.) may be beneficially used. The ratio of the natural carbohydrates may be properly determined by selection of those skilled in the art.

In addition, the health functional food composition of the present embodiment may contain various nutrients, vitamins, minerals (electrolytes), flavors such as synthetic flavors and natural flavors, etc., coloring agents and mogul agents (cheese, chocolates, etc.), pectic acid and its salts, alginic acid and its salts It may contain an organic acid, protective colloidal thickeners, pH adjusting agents, stabilizers, preservatives, glycerin, alcohol, carbonated agents used in soft drinks, and the like. These components can be used independently or in combination. Ratio of these additives is also properly selected by those skilled in the art.

As other aspect of the present embodiment, the present embodiment provides a method for preventing or treating liver fibrosis comprising a step of administering a composition containing adipose stem cell-derived exosomes as an active ingredient to a subject.

Herein, "subject" means a subject in need of treatment for a disease, and more specifically means mammals such as human or non-human primates, mouse, rat, dog, cat, horse and cow, etc.

Hereinafter, in order to help understanding of the present embodiment, preferable examples are presented. However, the following examples are provided only for the purpose of easier understanding of the present invention, and the contents of the present invention are not limited by the following examples.

Example 1

Preparation of Human Adipose Stem Cell-Derived Exosomes, and Analysis and Evaluation of Physical and Biochemical Properties To isolate exosomes from human adipose stem cells, the human adipose stem cells were cultured in DMEM (Dulbecco's Modified Eagle Medium) medium (Gibco, Cat #: 11995065), and 24 hours before isolating exosomes, it was replaced by DMEM medium not comprising serum, antibiotics and phenol red (Gibco Cat #: 31053028), and it was cultured for 24 hours.

Afterwards, the cell culture supernatant was collected and the centrifugation was progressed under the condition of 4° C., 3000 xg for 10 minutes, and then cell debris and wastes were removed using a 0.2 μm filter. Then, from the culture solution, using Tangential Flow Filtration System (TFF System), exosomes were isolated and purified. Meanwhile, after collecting the culture supernatant from the human adipose stem cells and adding common culture medium DMEM again, cells were cultured, and such a process was repeated up to 8 times of subculture to isolate exosomes.

The physical and biochemical properties of exosomes isolated from human adipose stem cells through the above process (Adipose-derived stem cell exosome; A-Exo) were confirmed by an electrical microscope and nanoparticle tracking analyzer.

As a result, as shown in FIG. 1, it was confirmed that exosomes had a spherical average size of 200 nm or less, and through this, it was confirmed that exosomes were successfully isolated from human adipose stem cells.

Example 2

Evaluation of Immunofluorescence and Real-Time Polymerase Chain Reaction of Human Adipose Stem Cell-Derived Exosomes in Human Hepatic Stellate Cell In order to confirm the influence of exosomes isolated in Example 1 on a human hepatic stellate cell which was known to largely involved in spouting of collagen and liver fibrosis factors, etc. as activated by liver damage in the real liver fibrosis process, the evaluation of efficacy of anti-fibrosis was progressed using LX-2 that was a related cell line.

Specifically, in order to confirm the influence of human adipose stem cell-derived exosomes on the expression level of α-Smooth Muscle Actin(α-SMA) that was a fibrosis factor generated from a hepatic stellate cell activated by liver fibrosis, its degree was evaluated using an immuno-fluorescence method.

α-SMA is one of factors expressed in an activated hepatic stellate cell, and is known to be expressed in a greater amount as liver fibrosis is induced, and thus in the present experiment, the hepatic stellate cell line, LX-2 was seeded at $2\times10^5$ cells/well in DMEM medium treated with 1 ng/mL of TGF-α, and after culturing for 24 hours, it was washed once or twice with DPBS.

Then, after dispersing human adipose stem cell-derived exosomes at a concentration of $1\times10^6$ cells/mL, $1\times10^7$ exosomes/mL, respectively, they were treated at 2 mL/well and cultured for 48 hours. Afterwards, finally, Anti-actin α-Smooth Muscle (α-SMA, A2547, Sigma aldrich, USA) were treated and reacted for 12 hours, and then a secondary fluorescent antibody, Anti-Cyanine2 was reacted to complete a tissue slide, and its form was confirmed by Confocal laser microscopy.

As a result, as shown in FIG. 2, it was confirmed that the expression level of α-SMA was largely increased in the hepatic stellate cell activated by treating TGF-α1, and it could be seen that the expression level of α-SMA was significantly decreased as the treated concentration of human adipose stem cell-derived exosomes (TFG-β1: group treated with TGF-α1 only, A-Exosome (1×10$^6$) and A-Exosome (1×10$^7$): groups treated with human stem cell-derived exosomes at 1×10$^6$~10$^7$ exosomes/ml).

In addition, in order to quantitatively confirm the effect of anti-fibrosis of human adipose stem cell-derived exosomes for the activated hepatic stellate cell, LX2, the real-time polymerase chain reaction evaluation was progressed for fibrosis-related factors, α-SMA, Collagen 1 and MMP-2, and the mRNA expression level change after treating exosomes in liver fibrosis-related fibrosis factors, α-SMA, Collagen 1 and Matrix Metalloproteinase-2(MMP-2) was confirmed.

As a result, as shown in FIG. 3, it was confirmed that when activating the hepatic stellate cell by treating TGF-β1, the mRNA amount of fibrosis-related factors, α-SMA, Collagen 1 and MMP-2 was largely increased, but when treating human adipose-derived stem cell exosomes by concentration (10$^6$-10$^7$) under the same condition, it was significantly decreased, and it was confirmed that this tendency was more effective as the concentration of exosomes was increased (Control: group treated with PBS, TFG-β1: group treated with TGF-β1 only, A-Exosome (1×10$^6$)~A-Exosome (1=10$^7$): groups treated with human stem cell-derived exosomes at 1×10$^6$~10$^7$ exosomes/ml).

Example 3

Comparative Evaluation of in Vitro Anti-Fibrosis Efficacy of Human Adipose Stem Cell-Derived Exosomes and Human Other Tissue Stem Cell-Derived Exosomes In order to comparatively experiment the excellent anti-fibrosis effect of the human adipose stem cell-derived exosomes according to the present embodiment compared to human other tissue stem cell-derived exosomes, by preparing exosomes isolated from human bone-marrow stem cells (Bone-marrow stem cell exosome: B-Exosome) and human umbilical-cord stem cells (Umbilical-cord stem cell exosome: U-Exosome), respectively, they were comparatively evaluated through the immunofluorescence and real-time polymerase chain reaction experiments of Example 2.

As a result, as shown in FIG. 4, it was observed that the human adipose stem cell-derived exosomes significantly decreased the fluorescence of α-SMA than the human umbilical-cord stem cell-derived exosomes or human bone-marrow stem cell-derived exosomes, and it was confirmed that such a decrease of fluorescence was apparently exhibited as the concentration of exosomes was increased (A-Exosome (1×10$^6$)~A-Exosome (1×10$^7$): groups treated with human adipose stem cell-derived exosomes at 1×10$^6$~10$^7$ exosomes/ml, B-Exosome (1×10$^6$)~B-Exosome (1×10$^7$): groups treated with human bone-marrow stem cell-derived exosomes at 1×10$^6$~10$^7$ exosomes/ml, U-Exosome (1×10$^6$)~U-Exosome (1×10$^7$): groups treated with human umbilical-cord stem cell-derived exosomes at 1×10$^6$10$^7$ exosomes/ml).

Furthermore, this tendency was additionally demonstrated through quantitative RNA amount comparison. In particular, as shown in FIG. 5, it was confirmed that when treating the human adipose stem cell-derived exosomes (10$^7$), the RNA amount of Collagen 1 was more effectively reduced than human other tissue stem cell-derived exosomes (A-Exosome (1×10$^6$)~A-Exosome (1×10$^7$): groups treated with human adipose stem cell-derived exosomes at 1×10$^6$~10$^7$ exosomes/ml, B-Exosome (1×10$^6$)~B-Exosome (1×10$^7$): groups treated with human bone-marrow stem cell-derived exosomes at 1×10$^6$~10$^7$ exosomes/ml, U-Exosome (1×10$^6$)~U-Exosome (1×10$^7$): groups treated with human umbilical-cord stem cell-derived exosomes at 1×10$^6$~10$^7$ exosomes/ml).

Through the above experiment, it could be seen that the human adipose stem cell-derived exosomes alleviated liver fibrosis effectively by lowering numerical values of fibrosis-related factors of a hepatic stellate cell activated by fibrosis than the human other tissue stem cell-derived exosomes.

Example 4

Evaluation of in Vivo Distribution Movements of Human Adipose Stem Cell-Derived Exosomes in Liver Fibrosis Animal Model In order to evaluate in vivo distribution movements of human adipose stem cell-derived exosomes, human adipose stem cell-derived exosomes, which were labeled with DiR; 1,1'-Dioctadecyl-3,3,3',3'-Tetramethylindotricarbocyanine lodide fluorescent materials, were dispersed in a culture solution 100 μL and injected into the tail vein in normal model and liver fibrosis-induced model mice. Then, after 24 hours, mice of each group were dissected and major organs were excised to confirm fluorescence thereof.

As a result, as shown in FIG. 6, it was confirmed that the largest amount of exosomes per unit area were accumulated in both normal model and liver fibrosis-induced model, and the larger amount of exosomes were confirmed in the liver fibrosis model than the normal model. This is thought to be due to a large number of hepatic stellate cells differentiated during the activation process by fibrosis (Hien T. T et al., Small 2015;19:2291-2304).

Example 5

Evaluation of Therapeutic Efficacy of Human Adipose Stem Cell-Derived Exosomes in Liver Fibrosis Animal Model Whether the anti-fibrosis effect was present in the real liver fibrosis animal model was confirmed using the human adipose stem cell-derived exosomes of Example 1, and it was confirmed that the liver function was more effectively improved, when administering human adipose stem cell-derived exosomes (A-Exosome) than human adipose stem cells (Adipose Derived Stem Cells, ADSC).

Specifically, as the animal experiment mimetic diagram of FIG. 7, a liver fibrosis model was manufactured by intraperitoneally administering TAA (Tioacetamine) that was a drug known to induce liver fibrosis at a concentration of 200 mg/kg with normal C57BL/6 mouse 3 times a week for 12 weeks. After 12 weeks, after intravenously administering exosome samples by setting the concentration to 1×10$^7$, 1×10$^8$, the liver fibrosis therapeutic effect was demonstrated.

At first, to conduct liver function examination according to administration of exosomes, after administering 1×10$^7$ and 1×10$^8$ exosomes into the liver fibrosis mouse model 3 times, respectively, by collecting blood after 5 days, the blood biochemical analysis was progressed. The collected blood was centrifuged at 4500 rpm for 15 minutes at 4° C., and then the supernatant was collected, and the liver function examination was requested to Chemon Inc.

More specifically, using an automatic blood analyzer ADVIA2120, SIEMENS, USA), AST (Aspartate aminotransferase), ALT (Alanine aminotransferase), ALP (Alkaline phosphatase), TBIL (Total bilirubin) and TP (Total protein) numerical values which were biochemical indexes were measured. In addition, by measuring the weight of collected liver tissue and calculating the ratio of the weight of the liver tissue compared to the total body weight (Ratio of LW/BW), its efficacy was schematized.

As a result of measuring numerical values of the above enzymes in blood, as shown in FIG. 8, it was confirmed that they did not largely affect the liver function throughout the above enzymes when administering human adipose stem cells and human adipose stem cell-derived exosomes in the normal model (Normal: normal mouse model, Fibrosis: liver fibrosis-induced model, PBS: group administered with PBS, ADSC ($1\times10^5$): group administered with $1\times10^5$ human adipose stem cells, A-Exosome ($1\times10^7$)~A-Exosome ($1\times10^8$): groups administered with $1\times10^7$~$10^8$ human adipose stem cell-derived exosomes).

In the liver fibrosis model, compared to the group administered with PBS only, it was confirmed that the liver function was improved by administration of human adipose stem cells (Adipose Derived Stem Cells, ADSC) and human adipose stem cell-derived exosomes (A-Exosome), and in particular, it could be confirmed that the liver function was more effectively improved, when administering $1\times10^8$ A-Exosomes three times than ADSC ($1\times10^5$ cells). In addition, by observing that the weight of liver compared to the total weight also had a value of ratio close to the normal animal model, it was confirmed that the fibrosis of liver tissue was effectively inhibited.

On the other hand, to progress liver tissue visual examination and pathological analysis, the liver of the mouse after the experiment was extracted and fixed with 4% neutral buffer formalin and embedded with paraffin, and then a 4 μm thickness of tissue fragments were manufactured, and H&E (Hematoxylin-Eosin) staining, α-Smooth Muscle Actin (α-SMA) and Masson's trichrome staining were conducted, and then it was observed with an optical microscope.

As a result, as shown in FIG. 9a, when observing the extracted liver with naked eyes, it was confirmed that human adipose stem cells (ADSC ($1\times10^5$)) and human adipose stem cell-derived exosomes (A-Exosome ($1\times10^7$-$10^8$)) administered into the normal model did not affect the tissue form of the liver. In addition, in the liver fibrosis model, it could be confirmed that the surface color and morphological changes were observed in the group administered with PBS only, whereas in the group administered with $1\times10^8$ human adipose stem cell-derived exosomes (A-Exosome ($1\times10^8$)), the color and tissue form were effectively maintained similar to those of normal liver tissue.

Meanwhile, H&E staining capable of confirming structural properties of cells in liver tissue of the liver fibrosis model, Masson's Trichrome (MT) staining capable of detecting collagen, and α-SMA staining for detecting myofibroblasts found in the fibrosis process were progressed.

As a result, as shown in FIG. 9b, when liver fibrosis was induced, it could be confirmed that necrosis was progressed as the cellular membrane of cells lost their shapes or were destroyed structurally. However, as shown in FIG. 9c, the collagen numerical value and α-SMA expression level increased by liver fibrosis were hardly observed in the normal model, and it was found that the amounts of α-SMA and Collagen were reduced in the group administered with $1\times10^8$ human adipose stem cell-derived exosomes (A-Exosome ($1\times10^8$)).

Through this, it could be concluded that the administration of human adipose stem cell-derived exosomes can effectively inhibit the formation of fibrous septa, as well as can maintain the form of normal liver tissue by maintaining the structural shape of hepatic cells and thereby inhibiting fibrosis of liver tissue.

Through the above experiment, it could be seen that the adipose stem cell-derived exosomes according to the present embodiment could exhibit an excellent liver fibrosis therapeutic effect in the liver fibrosis animal model, as genetic information, proteins and growth factors, etc. for treating liver fibrosis were contained therein, and the exosomes had advantages that they had good biocompatibility and excellent absorption rate, as they were cell-derived materials, and it could be seen that the adipose stem cell-derived exosomes according to the present embodiment could be usefully used for prevention, alleviation or treatment of liver fibrosis.

The afore-mentioned description of the present embodiment is for illustration, and it will be understood by those skilled in the art that it can be easily modified into other specific forms without changing the technical spirit or essential features of the present embodiment. Therefore, it should be understood the examples described above are illustrative in all respects and not limitative.

INDUSTRIAL APPLICABILITY

The adipose stem cell-derived exosomes according to the present embodiment can overcome limitations of therapeutic drugs used currently and minimize side effects by cancerization of stem cells or cell wastes that may be caused in the treatment using stem cells themselves.

In addition, since it can have an effect of reducing the treatment cost, as it can be naturally delivered to liver through simply applicable intravenous injection or local administration method without surgery, the adipose stem cell-derived exosomes according to the present embodiment may be usefully used for preventing, alleviating or treating liver fibrosis.

The invention claimed is:
1. A method for alleviating or treating liver fibrosis, comprising administering a composition comprising adipose stem cell-derived exosomes as an active ingredient to a subject in need thereof.
2. The method according to claim 1,
wherein the adipose stem cell is human adipose stem cell.
3. The method according to claim 1,
wherein the composition reduces a level of aspartate aminotransferase (AST), alanine aminotransferase (ALT), alkaline phosphatase (ALP), total bilirubin (TP), or LW/BW (Ratio of liver weight to body weight) in blood.
4. The method according to claim 1,
wherein the composition is a pharmaceutical or a food composition.

* * * * *